(12) United States Patent
Lee et al.

(10) Patent No.: US 11,116,172 B2
(45) Date of Patent: Sep. 14, 2021

(54) PENTAS PLANT HAVING A NOVEL TRAILING GROWTH HABIT

(71) Applicant: SYNGENTA PARTICIPATIONS AG, Basel (CH)

(72) Inventors: Jaemin Lee, Gilroy, CA (US); Jason Jandrew, Nipomo, CA (US); Amy Edmondson, Hollister, CA (US)

(73) Assignee: Syngenta Participations AG, Basel (CH)

( * ) Notice: Subject to any disclaimer, the term of this patent is extended or adjusted under 35 U.S.C. 154(b) by 127 days.

(21) Appl. No.: 15/756,612

(22) PCT Filed: Sep. 6, 2016

(86) PCT No.: PCT/US2016/050362
§ 371 (c)(1),
(2) Date: Mar. 1, 2018

(87) PCT Pub. No.: WO2017/048547
PCT Pub. Date: Mar. 23, 2017

(65) Prior Publication Data
US 2018/0184603 A1  Jul. 5, 2018

Related U.S. Application Data

(60) Provisional application No. 62/219,878, filed on Sep. 17, 2015.

(51) Int. Cl.
| | | |
|---|---|---|
| *A01H 6/76* | (2018.01) | |
| *A01H 5/02* | (2018.01) | |
| *A01H 1/02* | (2006.01) | |
| *A01H 1/04* | (2006.01) | |
| *A01H 3/00* | (2006.01) | |
| *A01H 5/04* | (2018.01) | |

(52) U.S. Cl.
CPC .............. *A01H 6/76* (2018.05); *A01H 1/02* (2013.01); *A01H 1/04* (2013.01); *A01H 3/00* (2013.01); *A01H 5/02* (2013.01); *A01H 5/04* (2013.01)

(58) Field of Classification Search
CPC ...................................................... A01H 6/76
See application file for complete search history.

(56) References Cited

U.S. PATENT DOCUMENTS

| | | | |
|---|---|---|---|
| PP19,055 P2 | 7/2008 | Shiotsuki | |
| 7,880,073 B2 * | 2/2011 | Dorr | A01H 5/10 435/410 |

OTHER PUBLICATIONS

Stritch, L, Plant of the Week, Partridge Berry (*Mitchella repens* L.), Webpage[online]. United States Department of Agriculture: Forest Service. Jun. 6, 2008 [retreived on Oct. 19, 2016]. <URL: http://fd.fed.us/wildflowers/plant-of-the-week/mitchella_repens.shtml>; p. 1, 1st-2nd paragraphs.
Nguyen et al., Journal of Heredity, 2008, 99, 6, 573-580.
(Syngenta) Starla[TM] Pentas Lanceolata. Product Datasheet [online]. May 2, 2015 [retrieved on Oct. 19, 2016]. Retrieved from the Internet: <URL: http://www.syngentaflowers.com/country/us/en/seeds/GrowingGuidelinesLib/pentas.pdf>; p. 1, title: p. 1, 1st column, 1st paragraph and 2nd column, 1st paragraph.
(Syngenta) Falling Star[TM] Pentas Culture Guide. Product Datasheet [online]. 2016[retrieved on Oct. 19, 2016]. Retrieved from the Internet: <URL: http://www.syngentaflowers.com/country/us/en/seeds/GrowingGuidelinesLib/Pentas-Falling-Star-Culture.pdf>; entire document.
International Search Report from International Application No. PCT/US2016/050362 dated Nov. 28, 2016.

* cited by examiner

*Primary Examiner* — David H Kruse
(74) *Attorney, Agent, or Firm* — Dale Skalla

(57) ABSTRACT

The present invention relates to a plant of the family Rubiaceae, in particular to a *Pentas lanceolata* plant having a novel trailing growth habit phenotype. Methods of obtaining, growing and propagating a plant of the invention and uses thereof are also provided. The invention further relates to pollen, seed and sexual as well as asexual progeny of such plants.

4 Claims, No Drawings

PENTAS PLANT HAVING A NOVEL TRAILING GROWTH HABIT

RELATED APPLICATION INFORMATION

This application is a 371 of International Application No. PCT/US2016/50362, filed Sep. 6, 2016, which claims priority to 62/219,878, filed Sep. 17, 2015, the contents of which are incorporated herein by reference herein.

FIELD OF THE INVENTION

The present invention relates to plants belonging to the family Rubiaceae, in particular to the species *Pentas lanceolata*, said plants having a novel trailing growth habit phenotype.

BACKGROUND

*Pentas* is a genus of plants in the family Rubiaceae. The plants have hairy green leaves and clusters of flowers in many different colors and shades. *Pentas* are attractive to butterflies and hummingbirds. Some species are commonly cultivated and can be grown in pots and baskets. Species such as *P. lanceolata* can withstand full sunlight and need little to no care, growing even in locations that are dry and hot.

A trailing growth habit is a highly desired trait for commercial *Pentas* plants. However, all current commercial *Pentas* cultivars grow upright and do not show trailing growth habit characteristics.

A *Pentas* plant having a trailing growth habit phenotype in different colors has been surprisingly developed from an upright plant. The trailing growth habit is unique and meets an unmet need amongst *Pentas* growers and end consumers. The trailing growth habit is maintained after the transition to flowering, and throughout the generative growth of the plant. The invention extends the spectrum of possible uses of *Pentas* in the gardening industry and is more appealing to the consumer.

SUMMARY OF THE INVENTION

The present invention provides a plant belonging to the family Rubiaceae, characterized in that said plant has a trailing growth habit phenotype during its vegetative and generative growth phase. In one embodiment, the present invention provides a plant belonging to the genus *Pentas*. In one embodiment, the present invention provides a plant belonging to the species *Pentas lanceolata*. In one embodiment, said present invention provides a plant belonging to an interspecific species which includes *P. lanceolata* in its ancestry.

There is provided a plant according to the invention, obtainable by crossing with *Pentas lanceolata* (T0402-1), representative seed of which has been deposited at NCIMB under deposit number NCIMB 42234.

In one embodiment, a plant according to the invention is a hybrid. In one embodiment, said plant is diploid. In one embodiment, said plant is tetraploid.

The present invention also provides a plant, wherein said plant is *Pentas lanceolata* (T0402-1), representative seed of which has been deposited at NCIMB under deposit number NCIMB 42234.

The present invention also provides a plant part of a *Pentas* plant according to the invention.

In one embodiment, said plant part is selected from the group consisting of propagated cuttings, seed and pollen.

There is also provided seed of a *Pentas* plant, wherein said seed when grown into a plant exhibits the trailing growth habit of a plant according to the invention.

There is also provided a method of growing a population of hybrid *Pentas* plants belonging to the species *Pentas lanceolata* comprising sowing seed and allowing said population of plants to grow and wherein said plants display a trailing growth habit phenotype.

There is also provided a method according to the invention for growing a plant as described above.

There is also provided the use of a *Pentas* plant or part thereof according to the invention. In one embodiment, said use is as a bedding plant. In another embodiment, said use is as a pot plant.

Definitions

The technical terms and expressions used within the scope of this invention are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants.

As used herein, the term "about" when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount or volume, as such variations are appropriate to perform the disclosed method.

As used herein, the term "breeding", and grammatical variants thereof, refer to any process that generates a progeny individual. Breeding can be sexual or asexual, or any combination thereof. Exemplary non-limiting types of breeding include crossings, selfing, doubled haploid derivative generation, and combinations thereof.

A "cultivated *Pentas* plant" or "elite *Pentas* plant" is understood within the scope of the invention to refer to a *Pentas* plant that is no longer in the natural state but has been developed by human care and for human use. "Cultivated plants" or "elite plants" are further understood to exclude those wild-type species which comprise the trait being subject of this invention as a natural trait and/or part of their natural genetics.

As used herein, the term "growing point" refers to a tip or edge of the plant. The distance between the furthest apart growing points of the plant represents the first width measurement as described in the examples section.

As used herein, the term "hybrid" in the context of plant breeding refers to a plant that is the offspring of genetically dissimilar parents produced by crossing plants of different lines or breeds or species, including but not limited to the cross between two inbred lines.

The phrase "inbred line" refers to a genetically homozygous or nearly homozygous population. An inbred line, for example, can be derived through several cycles of brother/sister breedings or of selfing. In some embodiments, inbred lines breed true for one or more pheno-typic traits of interest. An "inbred", "inbred individual", or "inbred progeny" is an individual sampled from an inbred line. The term "inbred" means a substantially homozygous individual or line.

The terms "introgression", "introgressed" and "introgressing" refer to a natural process whereby genomic regions of one species, variety or cultivar are moved into the genome of another species, variety or cultivar, by crossing those species. The process may optionally be completed by backcrossing to a recurrent parent.

A "plant" is any plant at any stage of development, particularly a seed plant or a vegetative plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, the phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "population" means a genetically heterogeneous collection of plants sharing a common genetic derivation. A population of plants typically corresponds to or more plants which have more or less the same phenotype at maturity in terms of the trailing growth habit phenotype of the invention.

As used herein, the term "progeny" refers to the descendant(s) of a particular cross. Typically, progeny result from breeding of two individuals, although some species (particularly some plants and hermaphroditic animals) can be selfed (i.e. the same plant acts as the donor of both male and female gametes). The descendant(s) can be, for example, of the F1, the F2, or any subsequent generation.

The phrases "sexually crossed" and "sexual reproduction" in the context of the present invention refer to the fusion of gametes to produce progeny (e.g., by fertilization, such as to produce seed by pollination in plants). In some embodiments, a "sexual cross" or "cross-fertilization" is fertilization of one individual by another (e.g., cross-pollination in plants). In some embodiments the term "selfing" refers to the production of seed by self-fertilization or self-pollination; i.e., pollen and ovule are from the same plant.

Within the meaning of the present invention, a plant with a "similar genetic background" refers to a plant, that is genetically closely related to a plant according to the invention and may be a parent in the pedigree of a plant according to the invention.

By "substantially higher number of branches", the number of branches in a trailing growth habit phenotype plant according to the invention is meant to be at least about 1.2 times, especially at least about 1.7 times, specifically between about 1.2 and about 1.9 times, higher than that found in a non-trailing growth habit type cultivar, which otherwise has a similar genetic background, when cultivated under the same rooting conditions and culturing conditions.

"Trait" is understood within the scope of the invention to refer to a characteristic or phenotype, for example a trailing growth habit phenotype. A trait may be inherited in a dominant or recessive manner, and may be monogenic or polygenic.

"Dominant" is understood within the scope of the invention to refer to an allele which determines the phenotype when present in the heterozygous or homozygous state.

A "recessive" allele is only displayed when present in the homozygous state.

DETAILED DESCRIPTION OF THE INVENTION

The present invention provides a plant belonging to the family Rubiaceae, characterized in that said plant is capable of displaying a trailing growth habit phenotype during its vegetative and generative growth phase. In one embodiment, the present invention is a cultivated plant belonging to the genus *Pentas*. In one embodiment, the present invention is a plant belonging to the species *Pentas lanceolata*. In one embodiment, the present invention is a plant which is a hybrid *Pentas*. In one embodiment, the present invention is a plant belonging to an interspecific species which includes *P. lanceolata* in its ancestry. In one embodiment, the present invention is a cultivated plant or an elite plant.

Within the meaning of the present invention, a trailing growth habit phenotype is a growth habit of a plant, in particular wherein the stems and lateral branches of the plant grow in predominantly horizontal orientation. A trailing growth habit type plant, in particular the deposited line described herein T0402-1, may also show a high degree of branching which is higher than that found in non-trailing growth habit type plants. If grown in the confinement of a plant container, the plant will extend over the container and, when reaching the edge of the container, also grow towards the ground. The internodes of a trailing-type plant according to the invention may optionally comprise adventitious roots, which are especially built at positions where the internodes get into contact with the substrate. Under favorable rooting conditions, the formation of adventitious roots is enhanced and may also occur without contact to the substrate.

Rooting conditions within the meaning of the present invention are typically characterized by moist substrate and temperatures of between 72-75 degree Fahrenheit (F), and a relative air humidity of between 80% to 90% during rooting.

In a further embodiment the plant according to the invention has a high degree of lateral branching which is substantially higher than that found in non-trailing growth habit type cultivars, even in cases wherein both plants otherwise have a similar genetic background.

In a specific embodiment the plant according to the invention has a trailing growth habit when measured after 4 weeks of rooting conditions followed by 12 weeks of standard culturing conditions.

The trailing growth habit phenotype of a plant of the invention can be expressed in terms of a ratio of plant height:plant width. In one embodiment, the ratio of plant height:plant width is 0.6 or less. In one embodiment, the ratio of plant height:plant width is 0.5 or less. In one embodiment, the ratio of plant height:plant width is 0.4 or less. In one embodiment, the ratio of plant height:plant width is 0.35 or less. In one embodiment, the ratio of plant height:plant width is between 0.3 and 0.6.

In one embodiment, a plant of the invention is capable of displaying the above ratio of plant height:plant width when grown under the following standard culturing conditions in a glasshouse for 12 weeks, typically in California, USA from early March until late May:

Pot positioned on ground, said pot having a dimension of 11 cm in width and 9.5 cm in height;

Plant growth Regulator B9 comprising Daminozide {butanedioic acid mono (2,2-dimethylhydrazide)};
Soil pH 6.5 to 6.8;
Average relative humidity of 63% to 66% (wherein the minimum relative humidity is equal or more than 27% and the maximum relative humidity is equal or less than 86%);
Average temperature of 65 to 67 Fahrenheit i.e. 18.3 degrees Celsius to 19.5 degrees Celsius (wherein the minimum temperature is equal or more than 59 Fahrenheit and the maximum temperature is equal or less than 89 Fahrenheit, i.e. 15.0 degrees Celsius to 31.7 degrees Celsius).

The plant of the invention preferably does not exceed 22 cm in height, more preferably 21 cm in height, more preferably 20 cm in height, more preferably 19 cm in height, more preferably 18 cm in height, more preferably 17 cm in height.

In one embodiment, a plant of the invention has a ratio of plant height:plant width of between 0.3 and 0.6, wherein the plant is between 16 cm to 20 cm in height.

In one embodiment, a plant of the invention has a ratio of plant height:plant width of 0.6 or less, wherein the plant does not exceed 20 cm in height.

In one embodiment, a plant of the invention has a ratio of plant height:plant width of 0.6 or less, wherein the plant does not exceed 18 cm in height.

In one embodiment, a plant of the invention has on average 8 or more branches.

In one embodiment, a plant of the invention has an average foliage length of 8 cm or less.

In one embodiment, a plant of the invention displays one of the above ratios of plant height:plant width, one of the above plant heights, one of the above number of branches and one of the above foliage lengths when said plant is grown under the standard culturing conditions above.

In one embodiment, the present invention provides a plant belonging to the genus *Pentas*.

In one embodiment, the present invention provides a plant belonging to the species *Pentas lanceolata*. In one embodiment, said plant is belonging to an interspecific species which includes *P. lanceolata* in its ancestry.

There is provided a plant according to the invention, obtainable by sexual crossing with *Pentas lanceolata* (T0402-1), representative seed of which has been deposited at NCIMB under deposit number NCIMB 42234.

In one embodiment, a plant according to the invention is a hybrid. In one embodiment, said plant is diploid. In one embodiment, said plant is tetraploid.

In one embodiment, the trailing growth habit phenotype is monogenic. In one embodiment, the trailing growth habit is a dominant trait. In one embodiment, the trailing growth habit is an incomplete dominant trait.

The present invention also provides a plant, wherein said plant is *Pentas lanceolata* (T0402-1), representative seed of which has been deposited at NCIMB under deposit number NCIMB 42234.

The present invention also provides a plant having a trailing growth habit phenotype, wherein said trait is the same as that found in *Pentas lanceolata* (T0402-1), representative seed of which has been deposited at NCIMB under deposit number NCIMB 42234.

There is provided a plant according to the invention, obtainable by crossing with *Pentas lanceolata* (T0402-1), representative seed of which has been deposited at NCIMB under deposit number NCIMB 42234.

The present invention also provides a plant part of a *Pentas* plant according to the invention.

In one embodiment, said plant part is selected from the group consisting of propagated cuttings, seed, pollen and plant cell.

There is also provided seed of a *Pentas* plant, wherein said seed when grown into a plant exhibits a trailing growth habit phenotype.

There is also provided a method of growing a population of hybrid *Pentas* plants belonging to the species *Pentas lanceolata* comprising sowing seed and allowing said population of plants to grow and wherein said plants display a trailing growth habit phenotype.

There is also provided a method according to the invention for growing a plant as described above.

There is also provided the use of a cultivated or elite *Pentas* plant or part thereof according to the invention. In one embodiment, said use is as a bedding plant. In another embodiment, said use is as a pot plant. In one embodiment, said use is in a hanging basket.

A further embodiment of the invention is a method of selecting a trailing *Pentas lanceolata* plant according to the invention comprising the steps of
a) growing back crossed *Pentas lanceolata* plants or sexual or asexual progeny thereof in rows in a field; and
b) selecting an individual plant or a group of plants which is capable of covering the free area between the rows significantly faster than the average of all plants grown in step a).

A further embodiment of the invention is an *Pentas lanceolata* plant having a trailing growth habit which is obtainable by a method as described above.

A further embodiment of the invention is a method of producing seed of a plant having a trailing growth habit comprising the steps of
a) obtaining a trailing growth habit plant according to the invention;
b) allowing said plant of step a) to i) self-pollinate or ii) sib pollinate or iii) cross-pollinate; and
c) harvesting seed resulting from step b).

A further embodiment of the invention is a method of producing a plant having a trailing growth habit comprising the steps of
a) obtaining a trailing growth habit plant according to the invention; and
b) asexually propagating said plant of step a).

A further embodiment of the invention is a method of producing a plant having a trailing growth habit comprising the steps of
a) planting a seed of a trailing growth habit plant according to the invention; and
b) growing said plant of step a).

Seed Deposit Details

Seed of the variety *Pentas lanceolata* (T0402-1) has been deposited and accepted under the terms of the Budapest Treaty on May 2, 2014 at the NCIMB, Craibstone, Aberdeen, UK under number NCIMB 42234 in the name of Syngenta Participations AG, Schwarzwaldallee 215, 4058 Basel, Switzerland.

The deposited variety represents a sufficient disclosure of a plant of the invention.

EXAMPLES

The following examples are presented in order to more fully illustrate some embodiments of the invention. They should in no way be construed, however, as limiting the broad scope of the invention. One skilled in the art can readily devise many variations and modifications of the principles disclosed herein without departing from the scope of the invention.

Example 1

Development of Trailing Growth Habit from Source Material

Development of the trailing growth habit started off from an upright white-flowered *Pentas* clone from the Syngenta breeding program. This clone was self pollinated. From the self pollinated seed, a three dot mass of white flowered plants was selected.

In the next generation, some plants were noticed that had a trailing growth habit. Two of these plants were selected and a two mass was made. The trailing growth habit came true from seed and was used in the next generation to cross out to different colors.

In 2006, Plant #990-(2) was crossed with a plant having a white flowered trailing growth habit.

In 2007, the same seed lot is sown as 1246 and 1247 and crossed again with the plant having a white flowered trailing growth habit. From population 1246, one selection (1246-1) was crossed with one selection (1247-1) from population 1247. 1246-1 crossed to white, pink and rose uprights was crossed with 1247-1 crossed to red, lavender and violet uprights.

In 2008, selections were made and self pollinated from F1 Hybrid seed.

In 2009, the F2 seed was grown out, selections were made and crosses and self pollinations were created.

In 2010, selections were made for future product.

Example 2

Morphological Comparison Between Plants of the Invention

The trailing growth habit phenotype is present in the white, pink bicolor, deep pink, rose and red colors.

The trailing growth habit phenotype displays monogenic and incomplete dominance. The trailing growth habit plant of the present invention is diploid.

Morphological comparisons were made between different colored *Pentas* plants of the invention made by development of the trailing growth habit from source material, each having the trailing growth habit phenotype. Average measurements were taken from 5 plants of each variety when the plants were aged 16 weeks from sticking. (Table 1). Plant height was measured from the soil level to the highest growing point for 5 plants and an average was taken. In order to measure plant width, two measurements were taken for each plant using a straight edge ruler. The first measurement involved identifying 2 growing points which were furthest apart on an imaginary straight line when looking down on the plant from above. The distance between these 2 growing points was measured. The second measurement involved identifying another 2 furthest apart growing points, wherein the imaginary straight line connecting these 2 growing points was at a 90 degree angle to the imaginary straight line between the first measured growing points. The first and second measurements were averaged for each of the 5 plants to provide plant width. The plant widths were then averaged.

The morphological comparisons are clearly showing that the trailing growth habit phenotype is consistently showing a plant height:plant width ratio of 0.6 or less for each of the different colors.

TABLE 1

Plant, foliage, branch and internode data comparison of different colored trailing growth habit *Pentas* plants of the invention

| | Plant height (cm) | Plant width (cm) | Foliage Width (cm) | Foliage length (cm) | Number of branch | Length of internode (cm) |
|---|---|---|---|---|---|---|
| Trailing *Pentas* White (T0402-1) | 16.50 | 29.20 | 3.12 | 7.74 | 8.80 | 5.78 |
| Trailing *Pentas* Pink Bicolor (T0403-1) | 19.7** | 45.7** | 3.9* | 7.90 | 10.7** | 5.1* |
| Trailing *Pentas* Deep Pink (T0403-2) | 17.2* | 39.7** | 3.6* | 8.03* | 8.70 | 5.13* |
| Trailing *Pentas* Rose (T0403-3) | 17.6* | 52.1** | 4.13** | 9.4** | 9.1* | 5.70 |
| Trailing *Pentas* Red (T0412-8) | 16.10 | 45.7** | 4.3** | 9.2** | 7.3* | 6.67** |

\*\*= statistical significance $P < 0.01$
\*= statistical significance $P < 0.05$.

Example 3

Morphological Comparison Between Plants of the Invention and Commercial *Pentas* Plants All commercially available *Pentas* plants are of the upright type and are all tetraploid or polyploid.

The following seed-based commercial *Pentas* plants were used in morphological comparison studies with a plant of the deposited variety NCIMB 42234. Results of the comparison studies are shown in Table 2.

The following commercial varieties were used for the morphological comparison: 'Graffiti' from Benary; 'Kaleidoscope' from Benary; 'Butterfly' from Pan American Seed; and 'Starla' from Syngenta.

Average measurements were taken from 10 plants of each variety. It can be seen that the ratio of plant height to plant width is much lower in the trailing growth habit plant of the invention compared with the upright commercial varieties. Foliage width and length is also significantly less compared with the commercial varieties (Table 2).

It can also be seen that the width and length of the trailing *Pentas* White (T0402-1) petals are shorter than the white commercial varieties (Table 3).

The deposited variety T0402-1 has a white color which is distinct from the commercially available varieties tested (Table 4).

TABLE 2

Plant, foliage, branch and internode morphological comparison of trailing growth habit Pentas with commercial Pentas with different genetic backgrounds

| | Plant height (cm) | Plant width (cm) | Foliage Width (cm) | Foliage length (cm) | Number of branch | Length of internode (cm) |
|---|---|---|---|---|---|---|
| Trailing Pentas White (T0402-1) | 16.00 | 28.50 | 3.00 | 7.57 | 8.67 | 5.63 |
| Graffiti White | 17.67** | 22.67** | 3.47* | 8.27* | 7.33 | 3.83** |
| Starla White | 33.67** | 22.33** | 4.7** | 12.03** | 5.33* | 7.00** |
| Butterfly White | 30.67** | 24.17** | 5.9** | 11.90** | 5.67* | 8.15** |
| Kaleidoscope Deep Red | 21.83** | 20.33** | 5.47** | 11.03** | 6.33* | 5.40 |
| Kaleidoscope Lilac | 25.17** | 17.67** | 4.93** | 10.63** | 6.67 | 6.93** |

TABLE 3

Flower and petal morphological comparison of trailing Pentas with commercial Pentas with different genetic backgrounds

| | Number of flower (per flolet) | Diameter of flower | Length of petal (cm) | Width of petal (cm) |
|---|---|---|---|---|
| Trailing Pentas White (T0402-1) | 58.53 | 1.76 | 0.73 | 0.40 |
| Graffiti White | 45.67** | 2.00** | 0.9** | 0.50** |
| Starla White | 68.67** | 1.73 | 0.77 | 0.60** |
| Butterfly White | 60.33 | 1.93* | 0.77 | 0.60** |
| Kaleidoscope Deep Red | 64.00 | 1.97* | 0.77 | 0.40 |
| Kaleiodoscope Lilac | 73.33** | 2.00** | 0.77 | 0.43 |

TABLE 4

Comparison of flower color by RHS color chart

| | RHS color |
|---|---|
| Trailing Pentas White (T0402-1) | 155B |
| Graffiti White | 155C |
| Starla White | 155A |
| Butterfly White | 155D |
| Kaleidoscope Deep Red | 53A |
| Kaleiodoscope Lilac | 72A |

The invention claimed is:

1. A plant belonging to the species *Pentas lanceolata* characterized in that said plant has a trailing growth habit phenotype, wherein the trailing growth habit phenotype is expressed in terms of a ratio of plant height to plant width of 0.5 or less, wherein the trailing growth habit is obtainable from the plant grown from the seed deposited under deposit number NCIMB 42234 wherein said plant is obtainable by crossing with *Pentas lanceolata* deposited line T0402-1, representative seed of which has been deposited at NCIMB under deposit number NCIMB 42234.

2. The plant according to claim 1, wherein said plant is a hybrid.

3. A plant part of the *Pentas* plant according to claim 1.

4. The plant part according to claim 3, wherein said plant part is selected from the group consisting of propagated cuttings, seed and pollen.

* * * * *